United States Patent [19]

Hoekstra et al.

[11] Patent Number: 6,071,691
[45] Date of Patent: Jun. 6, 2000

[54] MATERIALS AND METHODS FOR MODULATING DIFFERENTIATION

[75] Inventors: Merl F. Hoekstra, Snohomish, Wash.; Mathew J. Thayer, Portland, Oreg.

[73] Assignee: Oregon Health Science University, Portland, Oreg.

[21] Appl. No.: 09/067,284

[22] Filed: Apr. 27, 1998

[51] Int. Cl.$^7$ .............................. C12Q 1/00; C12Q 1/68; G01N 33/53
[52] U.S. Cl. ..................................... 435/4; 435/6; 435/7.1
[58] Field of Search ..................................... 435/325, 366, 435/377, 4, 6, 7.1

[56] References Cited

FOREIGN PATENT DOCUMENTS

WO 91/09955 of 0000 WIPO.
WO 92/20808 of 0000 WIPO.
WO 94/12650 of 0000 WIPO.
WO 97/18323 of 0000 WIPO.

OTHER PUBLICATIONS

Al–Khodairy, et al., "Identification and Characterization of New Elements Involved in Checkpoint and Feedback Controls in Fission Yeast," *Mol. Biol. Cell.* 5:147–160 (1994).

Andersen, et al., "Stem cell and transcription factors in the development of the mammalian neural crest," *FASEB, J.* 8:707–713 (1994).

Ausebel, et al., (Eds) *Protocols in Molecular Biology*, John Wiley & Sons (1994), pp. 9.6.3 through 9.6.12.

Bader and Fischman, "Immunochemical Analysis of Myosin Heavy Chain during Avian Myogenesis In Vivo and In Vitro," *J. Cell Biol.*, 95:763–770 (1982).

Barr, et al., "Rearrangement of the PAX3 paired box gene in the pediatric solid tumour alveolar rhadbomyosarcoma," *Nat. Genet.*, 3:113:117 (1993).

Benezra, et al., "The Protein Id: A Negative Regulator of Helix–Loop–Helix DNA Binding Proteins," *Cell*, 61:49–59 (1990).

Bishop, J.M., "The Molecular Genetics of Cancer," *Science* 235:305–311 (1987).

Budowle and Baechtel, "Modifications to improve the effectiveness of restriction fragment length polymorphism typing," *Appl. Theor. Electrophor* 1:181–187 (1990).

Carr, et al., "Control of cell cycle arrest by the Mec1$^{sc}$/Rad$^{sp}$ DNA structure checkpoint pathway," *Curr.Opin.Genet.Dev.* 7:93–98 (1997).

Carr, et al., "Checkpoints Take the Next Step," *Science*, 217:314–315 (1996).

Cher, et al., "Genetic Alterations in Untreated Metastases and Androgen–independent Prostate Cancer Detected by Comparative Genomic Hybridization and Allelotyping," *Cancer Res.*, 56:3091–3102 (1996).

Cimprich, et al., "cDNA cloning and gene mapping of a candidate human cell cycle checkpoint protein," *Proc.Nat'l.Acad.Sci.(USA)* 93:2850–2855 (1996).

Delihas, et al., "Natural antisense RNA/target RNA interactions: Possible models for antisense oligonucleotide drug design," *Nature Biotechnology* 15:751–753 (1997).

Dias, et al., "Myogenic Regulatory Protein (MyoD1) Expression in Childhood Solid Tumors: Diagnostic Utility in Rhabdomyosarcoma," *Am.J.Pathol.*, 137:1283–1291 (1990).

Donehower, et al., "Mice deficient for p53 and developmentally normal but susceptible to spontaneous tumors," *Nature*, 356:216–221 (1992).

Fakharzadeh, et al., "Tumorigenic potential associated with enhanced expression of a gene that is amplified in a mouse tumor cell line," *EMBO J.*, 10:1565–1569 (1991).

Favaloro, et al., "Transcription Maps of Polyoma virus–Specific RNA: Analysis by Two–Dimensional Nuclease A1 Gel Mapping," *Methods Enzymol*, 65:718–749 (1980).

Fiddler, et al., "Amplification of MDM2 Inhibits MyoD–Mediated Myogenesis," *Mol. Cell Biol.* 16:5048–5057 (1996).

Fiszman and Fuchs, "Temperature–sensitive expression of differentiation in transformed myoblasts," *Nature*, 254:429–431 (1975).

Flaggs, et al., "Atm–dependent interactions of a mammalian Chk1 homolog with meiotic chromosomes," *Curr. Biol.* 7(12):977–986 (1997).

Fournier, et al., "A general high–efficiency procedure for production of microcell hybrids," *Proc.Nat'l.Acad. Sci.(USA)* 78:6349–6353 (1981).

Friedman, et al., "Progress Toward Human Gene Therapy," *Science*, 244:1275–1281 (1989).

Fukasawa, et al., "Abnormal Centrosome Amplification in the Absence of p53," *Science* 271:1744–1747 (1996).

Hardy, et al., "Fibroblast Growth Factor Inhibits MRF4 Activity Independently of the Phosphorylation Status of a Conserved Threonine Residue within the DNA–Binding Domain," *Mol.Cell Biol.*, 13:5943–5956 (1993).

Hawley and Friend, "Strange bedfellows in even stranger places: the role of ATM in meiotic cells, lymphocytes, tumors, and its functional links to p53," *Genes Dev.*, 10:2383–2388 (1996).

Heselmeyer, et al., "Gain of chromosome 3q defines the transition from severe dysplasia to invasive carcinoma of the uterine cervix," *Proc.Nat'l.Acad.Sci.(USA)* 93:479–484 (1996).

Hiti, et al., "Expression of the MyoD1 Muscle Determination Gene Defines Differentiation Capability but Not Tumorigenicity of Human Rhabdomyosarcomas," *Mol.Cell Biol.*, 9:4722–4730 (1989).

Hoekstra, et al., "Responses to DNA damage and regulation of cell cycle checkpoints by the ATM protein kinase family," *Curr.Opin.Genet.Dev.*, 7:170–175 (1997).

(List continued on next page.)

Primary Examiner—Robert A. Schwartzman
Attorney, Agent, or Firm—Marshall, O'Toole, Gerstein, Murray & Borun

[57] ABSTRACT

This invention generally relates to materials and methods for modulating the differentiation of cells. Specifically provided are methods to promote or inhibit cell differentiation and methods to identify compounds that promote cellular differentiation.

7 Claims, No Drawings

OTHER PUBLICATIONS

Holtzer, et al., "Effect on oncogenic virus on muscle differentiation," *Proc.Nat'l.Acad.Sci.(USA)* 72:4051–4055 (1975).

Keegan, et al., "The Atr and Atm protein kinases associate with different sites along meoitically pairing chromosomes," *Genes Dev.*, 10:2423–2437 (1996).

Lasser, et al., "Transformation by Activated ras or fos Prevents Myogenesis by Inhibiting Expressing of MyoD1," *Cell*, 58:659–667 (1989).

Li, et al., "FGF Inactivates Myogenic Helix–Loop–Helix Proteins through Phosphorylation of a Conserved Protein Kinase C Site in Their DNA–Binding Domains," *Cell*, 71:1181–1194 (1992).

Loh, et al., "Human chromosome 11 contains two different growth suppressor genes for embryonal rhabdomyosarcoma," *Proc.Nat'l.Acad.Sci.(USA)* 89:1755–1759 (1992).

Lugo, et al., "Isolation of Microcell Hybrid Clones Containing Retroviral Vector Insertions into Specific Human Chromosomes," *Mol.Cell.Biol.* 7:2814–2829 (1987).

Miller, et al., "Human gene therapy comes of age," *Nature* 357:455–460 (1992).

Mitchell, et al., "Molecular definition in a somatic cell hybrid of a specific 2:13 translocation breakpoint in childhood rhabdomyosarcoma," *Oncogene*, 6:89–92 (1991).

Morrison, et al., "Regulatory Mechanisms in Stem Cell Biology," *Cell*, 88:287–298 (1997).

Newsham, et al., "Microdissection of Chromosome Band 11p15.5: Characterization of Probes Mapping Distal to the HBBC Locus," *Genes Chromosom. Cancer*, 3:108–116 (1991).

Oliner, et al., "Amplification of a gene encoding a p53–associated protein in human sarcomas," *Nature*, 358:80 (1992).

Peterson, et al., "Negative Control of the Helix–Loop–Helix Family of Myogenic Regulators in the NFB Mutant," *Cell*, 62:493–502 (1990).

Porcher, et al., "The T Cell Leukemia Oncoprotein SCL/ta1–1 Is Essential for Development of All Hematopoietic Lineages," *Cell*, 86:47–57 (1996).

Rao, et al., "Ectopic Expression of Cyclin D1 Prevents Activation of Gene Transcription by Myogenic Helix–Loop–Helix Regulators," *Mol.Cell Biol.* 14:5259–5267 (1994).

Ried, et al., "Mapping of Multiple DNA Gains and Losses in Primary Small Cell Lung Carcinomas by Comparative Genomic Hybridization," *Cancer Res.*, 54:1801–1806 (1994).

Rotman and Shiloh, "The ATM Gene and Protein: Possible Roles in Genome Surveillance, Checkpoint Controls and Cellular Defense against Oxidative Stress," *Cancer Surv.* 29:285–304 (1997).

Savitsky, et al., "A Single Ataxia Telangiectasia Gene with a Product Similar to P1–3 Kinase," *Science*, 268:1749–1753 (1995).

Scrable, et al., "Rhabdomyosarcoma–associated locus and MYOD1 are syntenic but separate loci on the short arm of human chromosome 11," *Proc.Nat'l.Acad.Sci.(USA)* 87:2182–2186 (1990).

Skapek, et al., "Inhibition of Myogenic Differentiation in Proliferating Myoblasts by Cyclin D1–Dependent Kinase," *Science*, 267:1022–1024 (1995).

Speicher, et al., "Comparative Genomic Hybridization Detects Novel Deletions and Amplifications in Head and Neck Squamous Cell Carcinomas," *Cancer Res.*, 55:1010–1013 (1995).

Tapscott, et al., "Deficiency in Rhabdomyosarcomas of a Factor Required for MyoD Activity and Myogenesis," *Science* 259:1450–1453 (1993).

Taub, et al., "Transcriptional control of liver regeneration," *FASEB J.*, 10:413–427 (1996).

Trask and Pinkel, *Flow Cytometry*, Methods in Cell Biology, vol. 33: New York Academic Press (1990).

Verma, "Treatment of disease by introducing healthy genes into the body is becoming feasible. But the therapy will not reach its full potential until the genes can be coaxes to work throughtout life," *Scientific American* 68–84 (1990).

Weber–Hall, et al., "Gains, Losses, and Amplification of Genomic Material in Rhabdomyosarcoma Analyzed by Comparative Genomic Hybridization," *Cancer Res.*, 56:3220–3224 (1996).

Weintraub, et al., "Activation of muscle–specific genes in pigment, nerve, fat, liver, and fibroblast cell lines by forced expression of MyoD," *Proc.Nat'l.Acad.Sci.(USA)* 86:5434–5438 (1989).

Weintraub, et al., "The MyoD Family and Myogenesis: Redundancy, Networks, and Thresholds," *Cell*, 75:1241–1244 (1993).

Yunis and Chandler, "High–Resolution Chromosome Analysis in Clinical Medicine," *Prog.Clin.Pathol.*, 7:267–288 (1978).

Itoh et al. (1997) Gene expression of MASH–1, MATH–1, neuroD and NSCL–2, basic helix–loop–helix proteins, during neural differentiation in P19 embryonal carcinoma cells. Tohoku J. Exp. Med. 182:327–336, Aug. 1997.

Crouch et al. (1993) Ara–C treatment leads to differentiation and reverses the transformed phenotype in a human rhabdomyosarcoma cell line. Exp. Cell Res. 204:210–216, Feb. 1993.

Thulasi et al. (1996) Alpha2a–interferon–induced differentiation of human alveolar rhabdomyosarcoma cells: correlation with down–regulation of the insulin–like growth factor type I receptor. Cell Growth Differentiation 7:531–541, Apr. 1996.

MATERIALS AND METHODS FOR MODULATING DIFFERENTIATION

BACKGROUND OF THE INVENTION

Rhabdomyosarcomas are highly malignant tumors composed of primitive muscle cells (stem cells) having a low propensity to differentiate. Cells of this type are grouped by histologic and cytogenetic criteria as either embryonal or alveolar rhabdomyosarcomas. The two types are distinguished by detection in embryonal rhabdomyosarcomas of a loss of heterozygosity on the short arm of chromosome 11 encompassing 11p15.5 [Mitchell et al, *Oncogene*, 6:89–92 (1991)] and in alveolar rhabdomyosarcomas, of a balanced translocation between chromosomes 2 and 13, t(2:13) (q35;q14) [Barr et al., *Nat. Genet.*, 3:113–117 (1993)]. Loss of heterozygosity at 11p15.5 is also associated with a number of other solid tumors [Newsham et al., *Genes Chromosom. Cancer*, 3:108–116 (1991)] suggesting the location of a tumor suppressor gene(s) for multiple tumor types in this region.

In tumor cells, expression of the muscle differentiation factor MyoD [Weintraub, H., *Cell*, 75:1241–1244 (1993)] has been shown to be a highly sensitive marker for classifying sarcomas as rhabdomyosarcomas [Dias et al., *Am. J. Pathol.*, 137:1283–1291 (1990); Scrable et al., *Proc. Natl. Acad. Sci., USA*, 87:2182–2186 (1990)]. MyoD is a member of a large family of transcription factors that belong to the basic-helix-loop-helix (BHLH) family known to control cell fate determination and stem cell function. While MyoD is associated with myoblast differentiation, related proteins determine the fate of other primitive cell types. For example, SCL controls Hematopoietic stem cell differentiation [Porcher, et al., *Cell* 86:47–57 (1996)] and neurogenic stem cell differentiation is controlled by the BHLH proteins MASH, neurogenin, and neuro D [Reviewed in Morrison et al., Cell 88:287–298 (1997) and Andersen, *FASEB J.*, 8:707–713 (1994)]. Similarly, liver stem cell differentiation is regulated by a combination of transcription factors including NF-κB, Stat3, and C/EBP [Taub, *FASEB J*. 10:413–427 (1996)]. Conversely, expression of transforming oncogenes inhibits cellular differentiation in several different cell lineages [Holtzer et al., *Proc. Natl. Acad. Sci. USA*, 72:4051–4055 (1975); Lassar et al., *Cell*, 58:659–667 (1989)]. In muscle cells, for example, expression of oncogenic tyrosine kinases (v-src and v-fps), growth factor receptors (v-erbB), nuclear oncogenes (v-myc, c-myc, v-erbA, E1A, and MDM2), and the activated form of signal transducing G proteins (H-ras and N-ras) can inhibit terminal differentiation to varying degrees [Fiszman and Fuchs, *Nature*, 254:429–431 (1975); Holtzer et al., *Proc. Natl. Acad. Sci. USA*, 72:4051–4055 (1975); Fiddler et al., *Mol. Cell Biol.* 16:5048–5057 (1996)]. The paradox that MyoD, shown to induce muscle differentiation in a wide variety of primary cells and transformed cell lines [Weintraub et al., *Proc. Natl. Acad Sci.*, 86:5434–5438 (1989)], serves as a hallmark for identification of a particular tumor type may be resolved by the possibility that MyoD appears to be non-functional in the neoplastic cells.

In rhabdomyosarcomas, abnormalities in protein expression have been reported, including for example, p53 and ras expression [Hiti et al., *Mol. Cell Biol.*, 9:4722–4730 (1989); Dias et al., *Am. J. Pathol.*, 137:1283–1291 (1990), Loh et al. *Proc. Natl. Acad Sci. USA*, 89:1755–1759 (1992)], however, the loci involved in the 11p loss of heterozygosity have not been identified. It is clear, however, that MyoD expression is unaffected [Scrable et al, *Proc. Natl. Acad Sci., USA*, 87:2182–2186 (1990)]. Chromosome transfer experiments wherein a normal chromosome 11 was introduced into rhabdomyosarcoma cells resulted in inhibition of cell growth and tumor formation in nude mice but had no effect on myogenic differentiation [Loh et al., *Proc. Natl. Acad. Sci. USA*, 89:1755–1759 (1992)]. Thus, the loss of the chromosome 11 locus was shown not to be responsible for the lack of differentiation in embryonal rhabdomyosarcomas.

One obvious phenotype of rhabdomyosarcomas is a lack of terminal differentiation and somatic cell genetic experiments have been carried out in attempts to identify genetic loci present in rhabdomyosarcoma cells that inhibit muscle differentiation. Results indicated that rhabdomyosarcomas could be classified by cell fusion experiments as either recessive or dominant with respect to their inability to differentiate [Tapscott et al., *Science*, 259:1450–1453 (1993)]. Furthermore, transfer of a derivative chromosome 14 from the rhabdomyosarcoma cell line Rh18, a cell type that displays a dominant non-differentiating phenotype, into the differentiation competent myoblast cell line C2C12 inhibited muscle differentiation as well as the ability of MyoD to transactivate reporter constructs. The derivative chromosome 14 contained amplified DNA originating from chromosome 12q13–14, a region containing several genes often amplified in sarcomas. Testing the amplified genes for the ability to inhibit muscle-specific gene expression indicated that forced expression of one gene in particular, Murine Double Minute Gene 2 (MDM2), inhibited MyoD function and consequently inhibited muscle differentiation [Fiddler et al., *Mol. Cell Biol.* 16:5048–5057 (1996)]. MDM2 was originally identified in a spontaneously transformed cell line [Fakharzadeh et al., EMBO J., 10:1565–1569 (1991)] and was subsequently shown to interact with p53 [Oliner et al., *Nature*, 358:80 (1992)].

In addition to the above chromosomal abnormalities, chromosome 3q alterations have been found to occur frequently in rhabdomyosarcomas. Previous studies have shown that gain of 3q was present in two out often embryonal rhabdomyosarcomas [Weber-Hall et al., *Cancer Res.*, 56:3220–3224 (1996)]. In addition, gain of 3q has been observed at high frequency in several other types of tumors, including, for example, 52% of prostate tumors [Cher et al., *Cancer Res.*, 56:3091–3102 (1996)], ten out of thirteen small cell lung carcinomas [Ried et al., *Cancer Res.*, 54:1801–1806 (1994)], ten out of thirteen head and neck squamous cell carcinomas [Speicher et al., *Cancer Res.*, 55: 1010–1013 (1995)], and nine out of ten cervical carcinomas [Heselmeyer et al., *Proc. Natl. Acad. Sci. USA*, 93:479–484 (1996)]. Furthermore, the gain of chromosome 3q by isochromosome formation in HPV16-infected cells defines the transition from severe dysplasia to invasive carcinoma of the uterine cervix [Heselmeyer et al., *Proc. Natl. Acad. Sci. USA*, 93:479–484 (1996)].

Even though the precise consequences of the various rhabdomyosarcoma genetic changes are unclear, the chromosomal rearrangement/damage is consistent with the belief that tumorigenesis is a multistep process with genetic damage occurring in most, if not all, cancer cells [Bishop, J. M., *Science*, 235:305–311 (1987)]. Whatever the precise mechanism involved, the prevalence of DNA damage in numerous cancer cells brings into question the role of cell cycle checkpoints in neoplastic cell types. Cell cycle checkpoints consist of signal transduction cascades which couple DNA damage detection to cell cycle progression and failure of one or more components in the system predisposes an individual to, or directly causes, many disease states such as cancer, ataxia telangiectasia, embryo abnormalities, and various immunological defects associated with aberrant B and T cell development. Polypeptides of the checkpoint system play roles in detecting and signaling a response to DNA damage that occurs as a result of replication errors, DNA mismatches, radiation damage, or chemotherapy.

It has been proposed that cell cycle checkpoints comprise at least three distinct classes of polypeptides which act sequentially in response to cell cycle signals or defects in chromosomal mechanisms. [Carr, A. M., Science, 271:314–315 (1996)]. The first class of proteins, exemplified by ATM [Rotman and Shiloh, Cancer Surv. 29:285–304 (1997)] and ATR [Keegan et al., Genes and Devel., 10:2423–2437 (1996)], detect or sense DNA damage or abnormalities. The second class of polypeptides, exemplified by Rad53. [Flaggs et al., Current Biology, (1997)], amplifies and transmits signals from the detector polypeptides. Finally, effector polypeptides, exemplified by mammalian p53, yeast weel, S. pombe CHK1, [Al-Khodairy et al., Mol. Biol. Cell, 5:147–160 (1994)], and human CHK1, bring about an appropriate cellular response, e.g. arrest of mitosis/meiosis or apoptosis.

Despite the roles for the checkpoint system to properly manage DNA damage and/or abnormalities, it is unclear what, if any relationship exists between the checkpoint system and neoplastic growth that results, at least in part, from genetic damage and/or rearrangement. More importantly, the art is silent with respect to what, if any relationship exists between expression of MyoD and the checkpoint system.

There thus is a need in the art for promoting differentiation of differentiation-inhibited cells such as rhabdomyosarcomas. More generally, there is also a need to modulate differentiation of other cells of interest. For example, inhibition of the differentiation of stem cells is contemplated so that the stem cell population may be expanded for therapeutic manipulation.

SUMMARY OF THE INVENTION

The present invention provides materials and methods for modulating cellular differentiation. The invention embraces in vitro, in vivo, and ex vivo methods wherein differentiation of a particular cell type can be induced or inhibited. The invention further contemplates methods and cell lines to identify compounds which induce or inhibit cellular differentiation.

In one aspect, the invention provides a method for inhibiting differentiation of a cell comprising the step of transforming or transfecting the cell with a polynucleotide encoding a cell cycle checkpoint protein. Cells inhibited in this manner can be expanded and are useful in therapeutic treatment of a variety of diseases requiring differentiation-inhibited cells including, for example, immunological diseases and diseases involving organ failure. Preferred cell types of the invention are either stably or transiently transformed or transfected with the cell cycle protein-encoding polynucleotide. Preferred cells contemplated by the invention are stem cells; most preferably cells of the invention are myoblasts. Other cell type contemplated by the invention include hematopoietic stem cells, neurogenic stem cells, liver stem cells, and germ cells. Preferred polynucleotides encode cell cycle checkpoint proteins ATR and CHK1 as well as other cell cycle checkpoint proteins including human isoforms of S. pombe Rad1, Rad 17, Cds1, Rad9, and Hus1.

In one aspect, cells of the invention are transiently or stably transformed or transfected with a polynucleotide encoding a cell cycle checkpoint protein. A preferred cell of the invention is C2(Rh30)-2, deposited on Jun. 25, 1998 with the American Type Culture Collection, 10801 University Boulevard, Manassas, Va. 20110 and assigned Accession Number CRL 12516. The introduction of polynucleotides encoding cell cycle checkpoint proteins can be accomplished by any of the multitude of methods well known and routinely practiced in the art, including, for example, precipitation techniques, electroporation, and vector-mediated transfection. In vector mediated transformation or transfection, the preferred vector is a viral vector. Preferred cells of the invention are stable transfectants.

As another aspect, the invention contemplates methods to identify compounds that enhance transcription from one or more polynucleotides encoding cell cycle checkpoint polypeptides, the method comprising the steps of (a) determining the degree of of a checkpoint polynucleotide in a host cell in the presence and absence of a test compound; (b) comparing the levels of transcription in (a); (c) identifying the test compound as a transcriptional enhancer when an increased level of transcription is observed in the presence of the compound. Host cells of the method include cells comprising endogenous genomic checkpoint polynucleotides, as well as host cells transformed or transfected with one or more polynucleotides encoding checkpoint polypeptides. The invention further embraces transcriptional enhancers identified by methods of the invention. The invention also contemplates methods to inhibit cell differentiation comprising the step of contacting a cell with a transcriptional enhancer of the invention.

Alternatively, the invention contemplates methods to identify compounds that enhance transcription from one or more reporter gene polynucleotides operatively linked to a cell cycle checkpoint polynucleotide regulatory sequence, the method comprising the steps of (a) determining the levels of expression of a reporter gene operatively linked to regulatory sequences normally associated with transcriptional control of checkpoint gene a host cell in the presence and absence of a test compound; (b) comparing the levels of expression in (a); (c) identifying the test compound as a transcriptional enhancer when an increased level of reporter gene expression is observed in the presence of the compound. Host cells of the method include cells transformed or transfected with cell cycle checkpoint regulatory polynucleotides operatively linked to any of a multitude of reporter gene well known and routinely utilized in the art. [See, for example, Ausebel, et al., (Eds), Protocols in Molecular Biology, John Wiley & Sons (1994), pp 9.6.3 through 9.6.12.] The invention further embraces transcriptional enhancers identified by methods of the invention. The invention also contemplates methods to inhibit cell differentiation comprising the step of contacting a cell with a transcriptional enhancer of the invention.

In another aspect, the invention provides methods to identify compounds that enhance biological activity of a cell cycle checkpoint polypeptide, the method comprising the steps of (a) determining the levels of activity of a checkpoint polynucleotide in a host cell in the presence and absence of a test compound; (b) comparing the levels of activity in (a); (c) identifying the test compound as a activity enhancer when an increased level of activity is observed in the presence of the compound. Host cells of the method include cells comprising endogenous genomic checkpoint polynucleotides, as well as host cells transformed or transfected with one or more polynucleotides encoding checkpoint polypeptides. The invention further embraces cell cycle checkpoint polypeptide activity enhancers identified by methods of the invention. The invention also contemplates methods to inhibit cell differentiation comprising the step of contacting a cell with an activity enhancer of the invention.

The invention further embraces methods to identify a compound that inhibits differentiation of a cell, said compound increasing transcription of a polynucleotide encoding a cell cycle checkpoint protein, said method comprising the steps of: a) determining the degree of differentiation of a cell line in the presence and absence of a test compound; b) comparing the degrees of differentiation in step a); and c) identifying the test compound that inhibits differentiation on the basis of a reduced degree of differentiation in the presence of the test compound and an increased level of transcription of the polynucleotide encoding the cell cycle checkpoint protein. The method further contemplates compounds identified by the methods of the invention.

The invention further provided a method for inhibiting differentiation of a cell comprising the step of contacting the cell with a compound that increases transcription of a polynucleotide encoding a cell cycle checkpoint protein. Preferred cells of the method are stem cells. The invention, however, further embraces myoblasts, hematopoietic stem cells, neurogenic stem cells, liver stem cells and germ cells The preferred checkpoint protein is ATR or CHK1.

The method also provides a method to identify a compound that inhibits differentiation of a cell, said compound increasing biological activity of a cell cycle checkpoint protein, said method comprising the steps of: a) determining the degree of differentiation of a cell line in the presence and absence of a test compound; b) the degrees of differentiation in step a); and c) identifying the test compound that inhibits differentiation on the basis of a reduced degree of differentiation in the presence of the test compound and an increased biological activity of the cell cycle checkpoint protein. The invention also embraces compounds identified by the method.

The invention also provides a method for inhibiting differentiation of a cell comprising the step of contacting the cell with a compound that increases biological activity of a cell cycle checkpoint protein. Preferred cells of the method are stem cells. Other cell types useful in the method include myoblasts, hematopoietic stem cells, neurogenic stem cells, liver stem cells and germ cells. The preferred checkpoint protein of the invention is ATR or CHK1.

Another aspect of the invention provides a method of promoting differentiation of a differentiation-inhibited cell comprising the step of contacting the cell with an inhibitor of a cell cycle checkpoint protein. In one aspect, the method embraces introducing into a cell a polynucleotide encoding a mutated cell cycle checkpoint polypeptide; the mutated polypeptide having a decreased biological activity thereby producing a dominant/negative phenotype in the cell. The method contemplates a compound which inhibits or reduces biological activity of the checkpoint protein. In another aspect, the invention contemplates a method for promoting differentiation in a differentiation-inhibited cell comprising the step of contacting the cell with a compound that inhibits or reduces transcription of a polynucleotide encoding a cell cycle checkpoint protein. Preferred differentiation-inhibited cell types are tumor cells. Most preferred differentiation-inhibited cells include rhabdomyosarcomas and actively proliferating cancer cells including, for example, cervical carcinomas, small cell lung tumors, prostate tumors, squamous cell carcinomas. Cells of the invention include those which are differentiation-inhibited by virtue of endogenous expression of a cell cycle checkpoint protein. Alternatively, cells of the invention can be modified by transformation to include a polynucleotide encoding one or more cell cycle checkpoint proteins. Cells of the invention also include those having increased copy number of one or more genes that maintain the differentiation-inhibited state, for example a rhabdomyosarcoma cell line having an isochromosome i(3q) resulting in an increase in copy number of the ATR gene. Differentiation of the differentiation-inhibited cells is achieved by contacting the cells with an inhibitor of a cell cycle checkpoint protein or an inhibitor of a protein downstream in the checkpoint cascade. Alternatively, differentiation is achieved by contacting the cell with a compound that inhibits transcription of (i) the cell cycle checkpoint protein, (ii) a transcription factor which acts to specifically increase transcription of the cell cycle protein, or (iii) the transcription of protein in a cell cycle checkpoint cascade modulated by a specific cell cycle protein. Conversely, exposing differentiated cell to increased cell cycle checkpoint proteins should revert these cells to a stem cell state or maintain a stem cell state for precursor cells.

Thus, the invention also contemplates methods for reverting differentiation of a differentiated cell comprising the step of contacting the differentiated cell with a compound that increases biological activity of a cell cycle checkpoint protein. In another aspect, the invention provides methods for reverting differentiation of a differentiated cell comprising the step of contacting the differentiated cell with a compound that increases transcription of a polynucleotide encoding a cell cycle checkpoint protein. In the preferred methods wherein the cell cycle checkpoint protein is selected from the group consisting of ATR and CHK1. In another aspect, the invention provides a method to revert differentiation of a muscle cell comprising the step of contacting the muscle cell with a compound that inhibits biological activity of MyoD.

The invention also contemplates methods for identifying a compound that promotes differentiation of a differentiation-inhibited cell, said compound inhibiting biological activity of a cell cycle checkpoint protein; said method comprising the steps of: a) determining the expression levels of a differentiation marker protein in said differentiation-inhibited cell in the absence and presence of the compound; b) comparing the expression levels of the differentiation marker determined in step a); and c) identifying the compound that promotes differentiation on the basis of the ability of the compound to promote increased expression level of the differentiation marker in the presence of the compound and to inhibit biological activity of the cell cycle checkpoint protein. As an alternative, the invention also include a method for identifying a compound that promotes differentiation of a differentiation-inhibited cell, said compound inhibiting transcription of a polynucleotide encoding a cell cycle checkpoint protein; said method comprising the steps of a) determining the expression levels of a differentiation marker protein in said differentiation-inhibited cell in the absence and presence of the compound; b) comparing the expression levels of the differentiation marker determined in step a); and c) identifying the compound that promotes differentiation on the basis of the ability of the compound to promote increased expression level of the differentiation marker in the presence of the compound and to inhibit transcription of the polynucleotide encoding the cell cycle checkpoint protein. The invention further provide compounds identified by the methods. Preferred differentiation mark protein of the methods are myosin heavy chain, MyoD, myogenin, and MLC/13. The invention further contemplates methods wherein the differentiation marker protein is SCL, MASH, neurogenin, neuroD, NF-κB or Stat3. The preferred cell cycle checkpoint polypeptide is either ATR or CHK1.

The invention further contemplates methods for promoting differentiation of a differentiation-inhibited cell comprising the step of modifying an endogenous gene sequence encoding a cell cycle checkpoint protein such that the cell expresses the cell cycle checkpoint protein at a reduced level. The targeted gene sequence can be modified in the protein coding region and/or in a transcriptional regulatory region. Modification of the polynucleotide can be effected in many ways. In one example, DNA encoding the cell cycle checkpoint protein is disrupted by insertions or deletions that result in a shift in the reading frame to the extent that expression of an active protein is no longer possible. Disruption of the DNA can take place in a region that regulates expression of the protein including promoter and/or enhancer sequences. Modification of the DNA in this manner can be effected by, for example homologous recombination. See, for example, PCT International Publication No. WO 94/12650, PCT International Publication No. WO 92/20808, and PCT International Publication No. 91/09955. Delivery of polynucleotides which can disrupt sequences in a cell is effected in vivo or ex vivo by use of vectors, and more particularly viral vectors (e.g., adenovirus, adeno-associated virus, or a retrovirus), or ex vivo by use of physical DNA transfer methods (e.g., liposomes or chemical treatments). For reviews of gene therapy technology see Friedmann, *Science*, 244:1275–1281 (1989); Verma, *Scientific American*: 68–84 (1990); and Miller, *Nature*, 357:455–460 (1992).

As an alternative, modification of the cell cycle checkpoint polynucleotide can be affected by hybridization with anti-sense sequences. The invention therefore contemplates a method for promoting differentiation of a differentiation-inhibited cell comprising the step of introducing into a cell a first polynucleotide encoding an anti-sense polynucleotide that hybridizes to a second polynucleotide encoding a cell cycle checkpoint protein. For a recent review of anti-sense therapy, see Delihas, et al., *Nature Biotechnology* 15:751–753 (1997). It is contemplated that antisense therapy could be applied to negatively regulate the expression of a cell cycle checkpoint protein. Antisense nucleic acids (preferably 10 to 20 base pair oligonucleotides) capable of specifically binding to expression control sequences or RNA are introduced into cells (e.g., by a viral vector or colloidal dispersion system such as a liposome). The antisense nucleic acid binds to the target sequence in the cell and prevents transcription or translation of the target sequence. Phosphothioate and methylphosphate antisense oligonucleotides are specifically contemplated for therapeutic use by the invention. The antisense oligonucleotides may be further modified by poly-L-lysine, transferrin polylysine, or cholesterol moieties at their 5' end.

The invention further provides methods to promote differentiation of a differentiation-inhibited cell comprising the step of contacting the cell with a compound that inhibits transcription of a polynucleotide encoding a cell cycle checkpoint protein. Alternatively, the invention embraces methods for promoting differentiation of a differentiation-inhibited cell comprising the step of introducing into the cell a polynucleotide encoding a mutated cell cycle checkpoint protein; said polynucleotide providing a dominant/negative phenotype in the cell. In both aspects, the preferred cell type is a tumor cell. A preferred tumor cell is selected from the group consisting of a rhabdomyosarcoma cell, a prostate tumor cell, a small cell lung carcinoma cell, a head squamous cell carcinoma cell, a neck squamous cell carcinoma cell, a cervical carcinoma cell, and a uterine cervix carcinoma cell.

Yet another aspect of the invention provides a method of identifying a compound that promotes differentiation of a differentiation-inhibited cell comprising the steps of (a) determining the expression levels of a differentiation marker protein in said differentiation-inhibited cell in the absence and presence of the compound; (b) comparing the expression levels of the differentiation marker determined in step a); and (c) identifying the compound that promotes differentiation on the basis of the ability of the compound to promote increased expression level of the differentiation marker in the presence of the compound. In the preferred method, the expression levels of differentiation marker proteins is determined in the absence and presence of a putative modulating compound. A increase in the expression of the marker protein in the presence of the compound indicates that the compound promotes differentiation. Differentiation-inhibited cells can be prepared by transiently or stably transfecting cells with a polynucleotide encoding a cell cycle checkpoint protein. In a preferred embodiment, cell of the invention are stem cell, and more preferably are myoblast cell type. In myoblasts, marker proteins include myosin heavy chain (MHC), MyoD, myogenin, or MLC1/3, and cell cycle checkpoint proteins ATR and or CHK1, as well as other proteins in the ATR cascade of proteins that effect cell cycle arrest. In hematopoietic stem cells, a marker protein is SCL; in neurogenic stem cells, MASH, neurogenin, and neuro D are exemplary markers; and in liver stem cells, marker proteins include NF-κB, Stat3, and C/EBP. In another preferred embodiment, cells of the method are rhabdomyosarcoma cells. In still another aspect, the preferred cell cycle checkpoint protein is either ATR or CHK1.

As another aspect, the invention provides a method to identify a compound that effects reversion of a differentiated cell type to a non-differentiated state comprising the steps of (a) determining the expression levels of a differentiation marker protein in said differentiated cell in the absence and presence of the compound; (b) comparing the expression levels of the differentiation marker determined in step (a); and (c) identifying the compound that promotes reversion to a non-differentiated state on the basis of the ability of the compound to promote decreased expression levels of the differentiation marker in the presence of the compound. Compound identified by the method may act by increasing biological activity of a cell cycle checkpoint polypeptide or increasing transcription from a polynucleotide encoding a cell cycle checkpoint polypeptide. Preferably, the cell cycle checkpoint protein is ATR or CHK1.

In still another aspect, the invention contemplates a method for promoting differentiation in a differentiation-inhibited cell type comprising the step of contacting the cell with a compound that increases biological activity of MyoD, or a member of the MyoD-like family of proteins. In one aspect, the compound acts directly or indirectly with the protein to increase biological activity. In another aspect, the compound act to increase transcription of polynucleotides encoding the protein. Preferred cells of the method are tumor cells; the preferred tumor cell is a rhabdomyosarcoma cell The invention also contemplates methods to identify a compound that promotes differentiation of a differentiation-inhibited cell, said compound increasing biological activity of MyoD, said method comprising the steps of: a) determining the expression levels of a differentiation marker protein in said differentiation-inhibited cell in the absence and presence of the compound; b) comparing the expression levels of the differentiation marker determined in step a); and c) identifying the compound that promotes differentiation on the basis of the ability of the compound to promote increased expression level of the differentiation marker in the presence of the compound and to increase biological activity of MyoD. The invention further embraces compounds identified by the method.

The expression levels of marker proteins can be determined by the methods well known in the art as well as those described herein. Exemplary methods include, but are not limited to, use of antibodies specific for proteins of interests, polynucleotide probes (DNA and RNA) which hybridize to the genes or mRNA encoding the differentiation marker proteins, or polynucleotides that bind to the encoded protein.

Cell cycle checkpoint protein inhibitors may be formulated in compositions comprising pharmaceutically acceptable carriers. Such compositions may additionally include chemotherapeutic agents. Dosage amounts indicated would be sufficient to result in inhibition of checkpoint protein activity in vivo. Inhibitors may include, for example, polypeptides or peptides which specifically bind to the checkpoint protein or checkpoint protein-encoding nucleic acid, oligonucleotides which specifically bind to the checkpoint protein or checkpoint protein-encoding nucleic acid, and/or other non-peptide compounds (e.g., isolated or synthetic molecules). The action of the inhibitor may directly affect a specific checkpoint polypeptide activity or underlying polynucleotide expression, or may alternatively affect activity of a polypeptide, or expression from its underlying polynucleotide, of some component downstream from a particular checkpoint polypeptide.

The invention also provides a method to determine differentiation potential of a cell comprising the step of measuring expression of a cell cycle checkpoint polypeptide in the cell, said cell with elevated expression of the cell cycle checkpoint polypeptide having a reduced potential to differentiate. The invention further includes methods to determine differentiation potential of a cell comprising the step of determining copy number of a checkpoint gene in the cell, said cell with multiple copies of the cell cycle checkpoint gene having a lower potential to differentiate

DETAILED DESCRIPTION OF THE INVENTION

The present invention is illustrated by the following examples. Example 1 describes identification of a dominant inhibitory locus in rhabdomyosarcomas. Example 2 reports on the isolation of isochromosome 3q from C2(Rh30)-2 Cells. In Example 3, abnormalities in the mitotic spindle and loss of G1 checkpoint control in i(3q) containing cells are described. Transfer of normal chromosome 3 into C2C12 cells is described in Example 4. Example 5 relates to forced expression of ATR that resulted in a phenocopy of the i(3q) containing cells. Examples 6 and 7 discuss results which show that forced expression of CHK1 in p53+ and p53- cells down-regulates expression of MyoD. Example 8 describes a screen for MyoD phosphorylation. Example 9 describes isolation of yeast and bacterial artificial chromosomes which encode ATR or CHK1.

EXAMPLE 1

Identification of Dominant Inhibitory Loci in Rhabdomyosarcoma Cells

Expression of MyoD, a protein required for differentiation of myoblasts, is characteristic of rhabdosarcoma cells despite the fact that the sarcoma cells do not differentiate. The inability of the rhabdosarcoma MyoD to induce differentiation may therefore be due to the presence of some inhibitory factor or the absence of some factor required for MyoD-induced differentiation.

It has previously been reported that heterokaryon formation with 10T1/2 cells can be used to classify different rhabdomyosarcoma cell lines as having either a recessive or a dominant inhibitory phenotype with respect to muscle differentiation [Tapscott et al., Science, 259:1450–1453 (1993)]. Three tumor cell lines, RD, Rh28, and RhJT, were identified which were capable of differentiating into muscle and it was proposed that these cell lines have a recessive non-differentiating phenotype that can be complemented by fusion with 10T1/2 cells. In contrast, one rhabdomyosarcoma cell line, Rh18, showed no differentiation following heterokaryon formation with 10T 1/2 cells indicating that the Rh18 cells contain a gene responsible for the dominant non-differentiating phenotype. It was later demonstrated that the Rh18 cells contain amplified MDM2 genes which were responsible for the dominant, non-differentiating phenotype [Fiddler et al., Mol. Cell Biol. 16:5048–5057 (1996)].

Heterokaryon formation with a fifth rhabdomyosarcoma cell line, Rh30, resulted in an intermediate phenotype in which only 30% of heterokaryons are capable of differentiation. Two possible explanations were contemplated for the intermediate phenotype of Rh30 cells. First, it is possible that Rh30 cells contain a dominant inhibitory locus which is present in only a subset of cells of the Rh30 cell population. The aneuploid nature of the cell line supports this possibility. Second, it is possible that the Rh30 cells have a recessive phenotype but a fraction of the cells in the Rh30 population have lost to capacity to express MyoD and myogenin. If this explanation were true, the MyoD and myogenin negative cells would no longer be able to induce myogenesis when fused to 10T1/2 cells. This cell line was therefore chosen to examine the inability of MyoD to induce differentiation in rhabdosarcoma cells.

To distinguish between the possibilities of a dominant inhibitory locus and a recessive phenotype, the presence of dominant inhibitory loci was first examined by transferring chromosomes from Rh30 cells into the differentiation competent myoblast cell line, C2C12 (ATCC No. CRL-1772) as follows. All cell lines discussed were grown in Dulbecco's modified Eagle's medium (DMEM) supplemented with 15% calf serum (Hyclone Laboratories) (growth medium). Rh30 cells were stably transfected with pRSVNEO by electroporation (300 volts, 960 μFD in PBS) (BioRad), and approximately 2,000 clones were pooled and expanded for use as donors in microcell fusions. Rh30 cells were micronucleated by adding 10.0 μg of colcemid per ml in DMEM plus 15% calf serum for 48 hours. The micronucleated cell populations were enucleated by centrifugation in the presence of 5 μg of cytochalasin B (Sigma) per ml and the isolated microcells were fused to C2C12 recipients as described previously [Fournier, Proc. Natl. Acad. Sci., USA, 78:6349–6353 (1981); Lugo et al. Mol. Cell Biol., 7:2814–2820 (1987)]. Microcell hybrid clones were isolated using cloning cylinders after three to four weeks of selection in medium containing 500 μg of Geneticin or G418 (Gibco) per ml. The resulting microcell hybrids, named the C2(Rh30) series, were isolated, expanded, and assayed for the ability to differentiate.

Myogenic differentiation of the hybrid cells was induced by growing cells to confluence followed by incubation in DMEM with 2% horse serum (differentiation medium). Northern blot analysis was performed by preparing total cytoplasmic RNA as described [Favaloro et al., *Methods Enzymol*, 65:718–749 (1980)]. Five micrograms total cytoplasmic RNA was used for Northern analysis on 1.5% agarose gels containing 6.7% formaldehyde. RNA was transferred to GeneScreen (DuPont) by capillary transfer in 10×SSC (1×SSC is 150 mM NaCl, 15 mM sodium citrate). RNA was cross linked by exposure to UV followed by baking at 80° C. for two to four hours. Blots were prehybridized for several hours at 42° C. in hybridization buffer (50% formamide, 1% bovine serum albumin [fraction V], 1 mM EDTA, 0.5 M sodium phosphate [pH 7.2], 5% sodium dodecyl sulfate [SDS]). Hybridization was carried out for twenty-four hours at 42° C. in fresh hybridization buffer containing $1 \times 10^8$ cpm of randomly primed [$^{32}$P]-labeled DNA probe comprising cDNA encoding MyoD, myogenin, MLC1/3 or CHO B [Fiddler et al., *Mol. Cell Biol.* 16:5048–5057 (1996)]. The filters were washed in 2×SSC-0.1% SDS for fifteen minutes at room temperature, 0.1× SSC-0.1% SDS for fifteen minutes at room temperature, and two changes of 0.1×SSC-0.1% SDS at 55° C. for fifteen minutes each. The blots were stripped for reuse by boiling for two minutes in double-distilled water.

Two out of nine hybrids, C2(Rh30)-2 and C2(Rh30)-21, expressed reduced levels of MyoD and myogenin mRNA as well as low levels of myosin light chain 1/3 (MLC1/3) mRNA. A similar analysis on an additional 10 hybrids identified a third non-differentiating hybrid, designated C2(Rh30)-7. The observations were consistent with the possibility that Rh30 cells contain a dominant inhibitory locus. While it is possible that the microcell hybrid clones C2(Rh30)-2, 7, and 21 represented non-differentiating variants of C2C12 cells, it is unlikely due to the low frequency of these variants in C2C12 populations [~$10^{-6}$; [Peterson et al., *Cell*, 62:493–502 (1990)] and due to the fact that in control fusions introducing chromosomes that do not inhibit myogenesis, non-differentiation hybrids were not observed [Fiddler et al., *Mol. Cell Biol.* 16:5048–5057 (1996)].

Because microcell fusion using rhabdomyosarcomas as donors often results in transfer of more than one human chromosome [Fiddler et al., *Mol. Cell Biol.* 16:5048–5057 (1996)], a second round of microcell fusions were performed in order to determine if the neo$^r$ insertions in each primary hybrid clone were linked to the inhibitory locus. C2(Rh30)-2, 7, and 21 were used as donors in microcell fusions with C2C12 cells as described above. The resulting secondary hybrids were assayed for muscle differentiation by visual inspection.

All of the secondary hybrids from C2(Rh30)-7 and C2(Rh30)-21 showed extensive myotube formation indicating that the neor insertions in these two primary clones were not linked to a dominant inhibitory loci. Furthermore, C2(Rh30)-7 and C2(Rh30)-21 contained multiple human chromosomes.

In contrast, 24 out of 30 colonies generated from C2(Rh30)-2 failed to show significant myotube formation. Ten secondary hybrids, designated C2(R302)-1 through -10, were isolated, expanded, and analyzed for expression of muscle-specific markers. Northern blot hybridizations, using MyoD, myogenin, and MLC1/3 as probes [Fiddler et al., *Mol. Cell Biol.* 16:5048–5057 (1996)] on RNA extracted from parental C2C12 cells and five of the secondary microcell hybrids indicated that four out of five hybrids (C2 (R302)-3, -4, -5, and -6) express low levels of MyoD, myogenin and MLC1/3 mRNA as compared to control C2C12 cells. Secondary C2(R302)-2 did not show reduced expression of MyoD, myogenin and MLC1/3. The results indicated that C2(Rh30)-2 cells contained a dominant inhibitory locus and that the locus was linked to the neo$^r$ marker.

EXAMPLE 2

Identification of Isochromosome 3q from C2 (Rh30)-2 Cells

To determine the human DNA content of C2(Rh30)-2, fluorescent in situ hybridization (FISH) with total human DNA as probe was performed as follows. DNA probes were nick-translated using standard protocols to incorporate biotin-11-dUTP or digoxigenin-dUTP. Slides of chromosomally normal male metaphase spreads were obtained from peripheral blood as previously described [Yunis and Chandler, *Prog. Clin. Pathol.*, 7:267–288 (1978)]. Hybridizations were carried out on slides at 37° C. for sixteen hours with probes at a concentrations from 40–60 ng/μl. Signal detection was carried out as described {Trask and Pinkel, *Flow Cytometry, Methods in Cell Biology*, Vol 33, New York Academic Press (1990)]. Amplification of the biotinylated probe signal utilized alternating incubations of slides with anti-avidin (Vector) and FITC-Extravidin (Sigma). Amplification of digioxygenated probes utilized alternating incubations of slides with FITC-tagged sheep antibodies generated in rabbit and FITC-tagged rabbit antibodies generated in sheep (Boehringer Mannheim). Slides were stained with propidium iodide (0.3 μg/ml), coverslipped, and viewed under UV fluorescence with FITC filers (Zeiss). Metaphase spreads showing probe signals were photographed with Fuji color film (ASA 100) at ASA 400. Identification of chromosomal loci were obtained by sequentially staining the same metaphase spreads with chromomycin A3/distamycin to produce fluorescent R-bands. R-banded metaphase spreads were then photographed with technical pan 2415 film (Kodak) at ASA 400. Because the C2C12 cells were of mouse origin and the human DNA probe derived from normal foreskin fibroblast cells did not hybridize to mouse DNA, the C2C12 chromosomes did not show any significant hybridization. However, hybridization to a single human chromosome was detected.

Analysis of G-labeled metaphase spreads [Yunis and Chandler, *Prog. Clin. Pathol.*, 7:267–288 (1978)] indicated that the human chromosome is an isochromosome 3q, i(3q), representing a reiteration of chromosome 3 bands q12–q26. FISH analysis indicated that i(3q) was present in the C2(R302) secondary hybrids that failed to differentiate and was absent from the hybrids that continued to differentiate.

In order to determine whether only chromosome 3 sequences were present on i(3q), FISH was performed with a chromosome 3-specific "paint" (Oncor, Gaithersburg, Md.) as probe. The results indicated that chromosome 3 sequences are present along the entire length of this chromosome and that i(3q) was derived from only chromosome 3 sequences. A similar analysis indicated that i(3q) was present in 50% of the parental Rh30 cells, indicating that a subset of the Rh30cells contained a dominant inhibitory locus.

In order to characterize chromosome 3 DNA present on i(3q), C2(Rh30)-2 cells and secondary hybrids were screened for specific DNA sequences known to reside on human chromosome 3. The primary microcell hybrid C2(Rh30)-2 and the four hybrids, C2(R302)-3, 4, 5 and 6, shown to include the inhibitory locus retained markers from 3q12–26. The one secondary hybrid, C2(R302)-2, that continued to differentiate did not retain any of these markers. The other two non-muscle primary hybrids C2(Rh30)-7 and C2(Rh30)-21 were shown to contain the i(3q) as assayed by chromosome 3 "paint" and PCR analysis.

In order to determine whether the ATR gene was present in the i(3q) containing hybrids, the following assay was carried out. PCR analysis as described above was conducted on genomic DNA isolated from C2C12 cells and the i(3q) containing hybrid C2(Rh30)-2 using human ATR-specific primers, oDH23 (SEQ ID NO: 1) and oDH26 (SEQ ID NO: 2)

```
Primer oDH23                              SEQ ID NO: 1
5' GACGCAGAATTCACCAGTCAAAGAATCAAAGAG 3'

Primer oDH26                              SEQ ID NO: 2
5' TGGTTTCTGAGAACATTCCCTGA 3'
```

High molecular weight DNA (100 ng) was used as template in the presence of 67 mM Tris (pH 8.8), 16 mM $(NH_4)_2SO_2$, 10 mM 2-mercaptoethanol, 6.7 µM EDTA, 2.0 mM $MgCl_2$, 10% glycerol, 0.2 mM dNTPs, 0.2 pM primers, 1.3 U Taq polymerase (Cetus). Following an initial four minute incubation at 96° C., samples were subjected to 35 cycles of 94° C. for thirty seconds, 55° C. for thirty seconds, and 72° C. for thirty seconds. Samples were separated on 30% agarose gels and stained with ethidium bromide.

Results indicated that the human ATR gene was present in the C2(Rh30)-2 DNA but not in C2C12 DNA. To determine whether the human ATR gene was present on both arms of the i(3q), therefore representing an increase in copy number, FISH analysis was performed as described above using ATR cDNA as probe. Results indicated the ATR gene was present on both arms of the i(3q).

EXAMPLE 3

Abnormalities in the Mitotic Spindle and Loss of G1 Checkpoint Control in i(3q)-Containing Cells Abnormal Mitotic Spindles During karyotypic analysis of the C2(Rh30) and C2(R302) hybrids, it was observed that the microcell hybrids containing the i(3q) contained many more mouse chromosomes than the parental C2C12 cells. Therefore, chromosomal counts on metaphase spreads from these microcell hybrids, as well as from C2C12 and the C2(3n) microcell hybrids containing normal human chromosome 3, were performed as previously described [Yunis and Chandler, *Prog. Clin. Pathol.*, 7:267–288 (1978)].

Results indicated that the parental C2C12 cells, as well as C2C12 microcell hybrids containing normal chromosome 3, displayed relatively stable tetraploid karyotypes with the majority of cells containing 76–85 chromosomes. In contrast, the microcell hybrids, C2(Rh30)-2, C2(Rh30)-21, C2(R302)-3, that retained i(3q) displayed aneuploid karyotypes with the majority of metaphase spreads containing greater than 156 chromosomes. Furthermore, metaphase spreads with greater than 300 chromosomes were observed in all three of the i(3q)-containing hybrids analyzed. These results indicated that introduction of the i(3q) into C2C12 cells caused the cells to become aneuploid, while transfer of normal chromosome 3 did not.

Because i(3q) caused a dramatic change in the chromosomal content of C2C12 cells, abnormalities in the mitotic spindle were examined by immunostaining with an antibody to β-tubulin. [Fukaswa et al., *Science*, 271:1744–1747 (1996)]. C2C12 cells contained a typical bipolar array of antiparallel microtubules organized at the poles in 98% of mitotic figures. In contrast, 58% of the mitotic C2(Rh30)-2 cells contain more than two spindles organized by multiple spindle poles. Abnormal numbers of centrosomes were present in the C2(Rh30)-2 cells as assayed by immunostaining with an antibody to γ-tubulin (Sigma, St. Louis, Mo.), while C2C12 cells contained one or two centrosomes per interphase cell. These results indicated that i(3q) caused abnormal centrosome amplification. Centrosome abnormalities of this type have previously been reported in the absence of p53 expression [Fukasawa et al., *Science*, 271:1744–1747 (1996)] suggesting that i(3q) inhibits normal p53 function.

Loss of G1 Checkpoint Control

Because the i(3q)-containing hybrids were found to have abnormal centrosome amplification similar to p53 null cells, and considering the role of p53 in cell cycle arrest at G1 [Donehower et al., *Nature*, 356:215–221 (1992)], it was decided to examine whether i(3q) modified the host cell's DNA damage-induced cell cycle checkpoints using C2C12 cells and the C2(R302) hybrids following γ-irradiation.

C2C12 cells and C2(Rh30)-2 cells were irradiated in a $^{137}Cs$ γ-irradiator at 100 rads/min (1 rad=0.01 Gy) for a total of 0 or 20 Gy and fed with fresh medium. After 17 hours, the cells were trypsinized, washed twice with 1% bovine serum albumin, and resuspended in 0.2 ml PBS. Cells were fixed by adding 5 ml of 70% ethanol at −20° C. Fixed cells were resuspended in 2 N HCl/0.5% Triton X-100 for thirty minutes at room temperature, and resuspended in 0.1 M $Na_2B_4O_7.10H_2O$ (pH 8.5) to neutralize the acid. Cells were stained with 5 ug/ml propidium iodide (Sigma) and analyzed on a FACS flow cytometer (Becton Dickinson Immunocytometry Systems) at laser excitation of 488 nm.

Results indicated that parental C2C12 cells retained a prominent G1 arrest mechanism following irradiation but that the hybrid C2(R302)-3, which contained the i(3q), contained two distinct abnormal features. First, the DNA content of the control C2(R302)-3 cells (which were not irradiated) was approximately twice that of the parental C2C12 cells. This observation was consistent with the previous observation that these cells contain approximately twice the number of chromosomes as the parental C2C12 cells. Second, the C2(R302)-3 cells contained a dramatic decrease in the G1 population following γ-irradiation indicating a lack of a functional G1 checkpoint similar to the phenotype in p53 null cells [Donehower et al., *Nature*, 356:215–221 (1992)]. The similarity suggested that i(3q) inhibited normal p53 function following DNA damage.

EXAMPLE 4

Transfer Of Normal Chromosome 3 Does Not Inhibit Myogenesis

In view of the identification of an inhibitory locus on i(3q) which is derived from chromosome 3 DNA, it was decided to examine whether normal human chromosome 3 contains a similar inhibitory locus.

Normal chromosome 3 was introduced into C2C12 cells by microcell fusion as described in Example 1 with GM11713 cells (Coriell Institute for Medical Research, Camden, N.J.), an A9 cell line retaining a single copy of normal human chromosome 3 into which a neo$^r$ gene has been inserted. Fused cells were identified by selecting for transfer of the chromosome 3 in G418. Resulting hybrid clones, designated the C2(3n) series, were isolated, expanded, and assayed (i) for the ability to differentiate into muscle by visual inspection for the presence of myotubes, and (ii) by Northern blot hybridizations using MyoD, myogenin, and MLC1/3 cDNAs as probes as described in Example 1.

Results from six clones examined indicated that, in addition to myotube formation, all of the C2(3n) hybrids expressed high levels of MyoD, myogenin and MLC1/3 mRNA. These observations indicate that transfer of normal human chromosome 3 into C2C12 cells did not inhibit muscle cell differentiation, and suggested that the phenotypic alterations observed in the i(3q) hybrids was due to genetic alterations that occurred in the generation of the abnormal rhabdomyosarcoma chromosome.

EXAMPLE 5

Forced Expression of ATR Results in a Phenocopy of Isochromosome i(3q)

The results described in the above examples indicate that a genetic alteration present on the i(3q) inhibits muscle differentiation and causes numerous cell cycle abnormalities when introduced into C2C12 cells. The results, however, did not permit identification of genes which participate in the inhibitory mechanism. Several hypotheses have been proposed to explain how the MyoD, as well as others in the family of proteins, are kept in check during proliferation: 1) inhibition of the MyoD family members by interaction with the Id family of negative HLH factors [Benezra et al., Cell, 61:49–59 (1990)], 2) inhibitory phosphorylation of the MyoD family members by protein kinase C [Li et al., Cell, 71:1181–1194 (1992); Hardy et al., Mol. Cell Biol., 13:5943–5956 (1993)], and 3) inhibition by cyclin-D dependent kinases [Rao et al., Mol. Cell Biol. 14:5259–5267 (1994b); Skapek et al., Science, 267:1022–1024 (1995)]. Because it is well known in the art to attempt to characterize genes identified by purely genetic approaches which may possibly participate is to analyze candidate genes that map to the identified chromosomal locus, oncogenes (e.g. ECT2, EVI1, FIM3, and BCL6), negative HLH factors (Hairy), and cell cycle related proteins (ATR and CDCL1) that map to 3q as candidate genes were considered for the muscle inhibitory locus. In view of the numerous cell cycle alterations observed in the i(3q) hybrids, one gene in particular was contemplated to be a likely candidate.

The ATR gene, which is related to ATM (ataxia telangiectasia mutated [Savitsky et al., Science, 268:1749–1753 (1995)] and is the human homolog of the Saccharomyces cerevisiae MEC1 and Schizosaccharomyces pombe Rad3 genes, has been mapped to 3q22–24 [Cimprich et al., Proc. Natl. Acad. Sci. USA, 93:2850–2855 (1996); Keegan et al., Genes Dev., 10:2423–2437 (1996)]. While there have not yet been any reports of mammalian phenotypes associated with ATR, mutations in the ATM gene lead to pleiotropic defects in cell cycle regulation following DNA damage, including loss of the G1/S and G2/M checkpoints [Hawley and Friend, Genes Dev., 10:2383–2388 (1996); Hoekstra, Curr. Opin. Genet. Dev., 7:170–175 (1997)]). In addition, mutations in either the S. cerevisiae MEC1 or the S. pombe RAD3 gene leads to similar defects in cell cycle checkpoint control [reviewed in Carr, A. M., Curr. Opin. Genet. Dev., 7:93–98 (1997)].

To determine whether ATR was involved in the non-differentiating phenotype and/or cell cycle abnormalities of the i(3q) containing hybrids, C2C12 cells were stably transfected with an expression vector encoding ATR as a fusion protein with a six histidine tag. Construction of the vector was carried out as follows.

PCR was carried out using primers MCCS6his (SEQ ID NO: 3) and ATR1R (SEQ ID NO: 4) that would incorporate sequences encoding the histidine tag to sequences encoding the amino-terminus of ATR. Amplification conditions included 100 ng PstA12 ATR template DNA,; 1×PCR buffer (Perkin Elmer, Cetus), 1.5 mM MgCl$_2$: 200 μM each dATP, dGTP, dCTP, and dTTP; 10 ng/μl each primer; 1 unit Taq polymerase (Perkin Elmer, Cetus).

```
MCCS6his                                                          (SEQ ID NO: 3)
5'-CGGGATCCAGCATGCATCACCATCACCATCACATGGGGGAACATGGGC-3'

ATR1R                                                             (SEQ ID NO: 4)
5'-CATGACCACTGGCCATTCCACACG-3
```

The reaction was first incubated at 94° C. for thirty seconds, followed by 25 cycles of 94° C. for thirty seconds, 60° C. for thirty seconds, and 72° C. for thirty seconds. The approximately 800 bp amplification product was digested with BamHI and MscI and ligated to two other fragments: a 10 kb fragment from pcDNAATR digested with BamHI and BstXI and an approximately 3 kb MscI to BstXI fragment containing the remainder of the ATR coding sequence. The resulting plasmid encoding a six-histidine tagged full length ATR molecule was designated pcDNA6his ATR.

C2C12 cells were transfected with pcDNA6hiSATR and grown in media containing G418 for three weeks to allow colonies to form, induced to differentiate in low serum media, and scored for muscle differentiation by immunostaining with a myosin heavy chain (MHC) antibody [Bader and Fischman, J. Cell Biol., 95:763–770 (1982)].

Control transfections, using empty expression vector, resulted in 100% of colonies (150/150) showing extensive cell fusion and positive staining with the MHC antibody. In contrast, 25% (50/200) of the colonies from the ATR transfected cells showed a dramatic reduction in MHC immunoreactivity.

To confirm the non-differentiating nature of these ATR transfected cells, and to test for cell cycle alterations, several non-fusing colonies, designated the C2ATR series clones, were isolated and expanded. Northern blot hybridizations to determine expression of MyoD, myogenin and MLC1/3 were carried out as described in Example 1 on RNA from two ATR transfected clones.

Two clones, C2ATR-1 and C2ATR-5, were found to express reduced levels of MyoD, myogenin and MLC1/3 mRNA as compared to parental C2C12 cells. Thus, the C2C12 cells transfected with the ATR expression vector have a phenotype similar to the i(3q) hybrids with respect to muscle differentiation. Chromosome counts on the two clones indicated the two contained aneuploid karyotypes similar to the i(3q) containing hybrids. Chromosome counts on C2C12 clones transfected with empty expression vector (C2cDNA1 and 2), all retained a stable tetraploid karyotype. Immunostaining C2ATR-1 and C2ATR-5 with the β and γ tubulin antibodies showed centrosome amplification leading to supernumerary spindles.

Forced expression of ATR therefore resulted in a phenocopy of the i(3q) containing hybrids, and that duplication of ATR by isochromosome formation caused loss of myogenic differentiation, abnormal centrosome amplification, and aneuploidy in the rhabdomyosarcoma cell line Rh30.

In order to determine if the i(3q) phenotype arose from rearrangement of the ATR encoding gene, Southern analysis was carried out as follows. High molecular weight DNA (10 µg) was digested to completion with HindIII and separated on 0.8% agarose gels in 0.04 M Tris acetate/2 mM EDTA. The DNA was transferred to Gene Screen (Dupont) membranes in 10×SSC (1×SSC is 150 mM NaCl, 15 mM Na-citrate), and UV crosslinked. Probes containing Alu sequences were processed and hybridized as described by Budowle and Baechtel, *Appl. Theor. Electorphor.* 1:181–187 (1990), to minimize background from repetitive sequences. The blots were stripped for reanalysis by incubation in 0.2N NaOH for thirty minutes.

Based upon the observations previously described in this Example, it proposed that the phenotypic consequences result from overexpression of ATR, is a consequence of chromosome duplication.

EXAMPLE 6

Forced Expression of ATR or CHK1 in C2C12 and NIH3T3 Cells Results in Down-Regulation of MyoD To test whether forced expression of ATR affects MyoD function, transient transfection assays were performed in NIH3T3 (ATCC No. CRL6361) cells co-transfected with MyoD and ATR. Cells were transiently co-transfected by the Lipofectamine (GibcoBRL) method. Approximately $3 \times 10_5$ cells were plated one day prior to transfection into 60 mm tissue culture plates. Transfection mixtures were comprised of 6 µg total DNA with 0.5 to 1.0 µg being the reporter construct. The lipid-DNA mixtures were added to the cells and brought to a final volume of 2 milliliters with serum free DMEM. The transfection mixture was allowed to sit on the cells for 6 hours after which the transfection solution was removed by aspiration. DMEM containing 15% calf serum was added to the cells, and the cells were harvested after approximately 48 hours.

CAT activity was measured using a phase extraction procedure. In brief, 48 hours after transfection, cell extracts were generated by freeze-thawing cell pellets in 100 µl 0.25 M Tris (pH 7.5). Following treatment at 65° C. for 15 min. to inactivate endogenous acetylases, 30 µl of extract was assayed with 0.2 mCi of [3H] chloramphenicol (Dupont-New England Nuclear) and 250 nM butyryl-CoA (Sigma), in a total volume of 100 µl. The reaction was allowed to proceed for 2 to 12 hours at 37° C. and stopped by mixing with 200 µl TMPD-Xylene (2:1) (Sigma). One hundred thirty microliters of the upper phase was removed and added to scintillation cocktail to be counted.

Co-transfecting increasing amounts of ATR expression vector inhibited the ability of MyoD to transactivate the MyoD dependent reporter construct 4RtkCAT, but had little affect on the ability of gal.VP16 to transactivate the GAL dependent reporter construct gal.CAT. These results suggested that ATR inhibited MyoD dependent transactivation.

Because CHK1 activity is dependent upon the ATR homolog, Rad3, in *S. pombe*, it was next tested whether forced expression of human CHK1 would result in the same phenotypes as the i(3q) and ATR. Initially, C2C12 (ATCC No. CRL 1772) cells were stably transfected with a pCINEO based (Invitrogen, San Diego) CHK1 expression vector using a BIORAD electroporator. Stable transfectants were selected in media containing G418, grown for three weeks to allow colonies to form, induced to differentiate in low serum media, and scored for muscle differentiation by immunostaining with a myosin heavy chain (MHC) antibody (Bader et al., 1982).

Control transfections, using empty expression vector (pCINEO), resulted in 100% (200/200) of colonies showing extensive cell fusion and positive staining with the MHC antibody. In contrast, 31% (62/200) of the colonies from the CHK1 transfection showed a dramatic reduction in MHC immunoreactivity.

To determine whether the CHK1 transfected clones contain cell-cycle abnormalities similar to the i(3q) hybrids, chromosome counts on two ATR stable lines, C2CHK-3 and C2CHK-4 were conducted. Similar to the i(3q) containing hybrids, these two clones contain aneuploid karyotypes. Immunostaining C2CHK-3 with the γ and β tubulin antibodies showed centrosome amplification leading to supernumerary spindles.

To examine whether forced expression of CHK1 also affects MyoD function, transient transfection assays were performed in NIH3T3 (ATCC No. CRL6361) cells co-transfected with MyoD and CHK1. Cells were transiently co-transfected by the Lipofectamine (GibcoBRL) method. Approximately $3 \times 10^5$ cells were plated one day prior to transfection into 60 mm tissue culture plates. Transfection mixtures were comprised of a total DNA content of 6 µg with 0.5 to 1.0 µg being reporter construct. The lipid-DNA mixtures were added to the cells and brought to a final volume of two milliliters with serum-free DMEM. The transfection mixture was allowed to sit on the cells for 6 hours after which the transfection solution was removed by aspiration. DMEM containing 15% calf serum was added to the cells, and the cells harvested after approximately 48 hours. CAT activity was measured using the phase extraction procedure described above.

Results indicated that co-transfecting increasing amounts of CHK1 expression vector inhibited the ability of MyoD to transactivate the MyoD dependent reporter construct 4RtkCAT, but had little affect on the ability of gal.VP16 to transactivate the GAL dependent reporter construct gal.CAT. Like ATR, therefore, forced expression of CHK1 inhibits MyoD dependent transactivation.

EXAMPLE 7

Forced Expression of A5 Cells Results in Down-Regulation of MyoD

Because the phenotype of cells containing the i(3q), as well as cells transfected with ATR or CHK1 display a phenotype very similar to p53 null cells [Donehower et al., *Nature* 365: 215–221 (1992); Fukasawa et al., *Science* 271:1744–1747 (1996)], it was tested whether the inhibition of MyoD activity by either ATR or CHK1 was dependent on p53 gene function.

A transient transfection assay in p53-/- mouse embryo fibroblasts (MEFs) [Donehower, et al. supra] was employed wherein cells were transiently co-transfected by the Lipofectamine (GibcoBRL) method. Approximately $3 \times 10^5$ cells were plated one day prior to transfection into 60 mm tissue culture plates. Transfection mixtures comprised 6 µg total DNA with 0.5 to 1.0 µg being reporter construct. The lipid-DNA mixtures were added to the cells and brought to a final volume of 2 milliliters with serum-free DMEM. The transfection mixture was allowed to sit on the cells for six hours after which the transfection solution was removed by aspiration. DMEM containing 15% calf serum was added to the cells, and the cells harvested after approximately 48 hours. CAT activity was measured using the phase extraction procedure described above.

Co-transfecting increasing amounts of CHK1 expression vector inhibited the ability of MyoD to transactivate the MyoD dependent reporter construct 4RtkCAT in the p53 null cells. In contrast, co-transfecting increasing amounts of ATR had no affect on the ability of MyoD to transactivate 4RtkCAT. These results indicated that inhibition of MyoD activity by ATR is p53 dependent but that CHK1 inhibition is not. The results also suggest that in the ATR cell cycle checkpoint pathway, p53 is downstream from ATR and upstream to CHK1.

EXAMPLE 8

MyoD Phosphorylation Assay

In order to screen for chemical modulators of ATR, a MyoD-based assay was developed as follows.

ATR was captured on a 96 well plate previously coated first with goat anti-mouse antibodies (Pierce) and secondly with anti-ATR antibody 224C. A hybridoma which secretes antibody 224C was deposited with the American Type Culture Collection (ATCC), 12301 Parklawn Drive, Rockville, Md. 20852 on Nov. 7, 1996 and assigned ATCC Accession Nos. HB 12233. The 224C antibody was added to the plate at a concentration of 2 mg/ml in BT blocking buffer and incubated for at least 30 hours at 4° C. The wells were washed with TBS containing 0.05% Tween 20 and mouse testes extract (prepared as described in Example 6 of WO 97/18323 published May 22, 1997 from International Application No. PCT/US96/19337, incorporated herein by reference) was added. Incubation was continued for an additional 20 hours at 4° C. The wells were washed again as before and a kinase reaction was carried out as follows.

A kinase reaction mixture, containing kinase buffer (as described in Example 6 of WO 97/18323), 10 μg ATP, 5 μCi $^{32}$P-γATP, and a peptide substrate, designated IDH22 (SEQ ID NO: 8) and derived from the MyoD protein, was added to each well and incubation carried out at room temperature for 40 minutes. The selection of this peptide substrate is described below.

IDH21 (SEQ ID NO: 9) included amino acids 119 through 130 and the second, IDH22. (SEQ ID NO: 8) comprised amino acid residues 132 through 146. Utilizing the kinase assay described above, it was observed that ATR phosphorylated IDH22 but not IDH21.

```
IDH21                                                    SEQ ID NO: 9
NH2-Arg-Arg-Arg-Leu-Ser-Lys-Val-Asn-Glu-Ala-Phe-Glu-COOH
```

EXAMPLE 9

Isolation of ATR Genomic Yeast Artificial Chromosomes and Genomic Bacterial Artificial Chromosomes and CHK1 Genomic Chromosome Pooled DNA samples from CEPH human yeast artificial chromosome (YAC) library and PRC1-11 bacterial artificial chromosome (BAC) library (both from Research Genetics, Huntsville Ala.) were screened to identify clones containing ATR or CHK1 coding regions. For both YAC and BAC cloning, pooled samples were amplified by PCR, and positive samples were used to identify subpools for second round amplification. Positive signals in the second amplification were used to identify master plates of individual YAC and BAC clones and a third amplification was carried out to identify individual clones. Conditions for the amplification reactions were as follows.

To identify YAC and BAC clones, PCR was carried out under conditions including 25 ng genomic DNA template, 80 pM primers (as set out below), 200 μM each nucleotide triphosphate, and 2.5 U AmpliTaq DNA polymerase (Perkin Elmer) in a reaction buffer containing 10 mM Tris-HCl (pH 8.3), 50 mM KCl, and 1 mM MgCl$_2$. Reactions included an initial incubation at 93° C. for four minutes, followed by 30 cycles of 93 ° C. for 30 seconds, 55° C. for 30 seconds, and 72° C. for 30 seconds, followed by a final incubation at 72° C. for seven minutes. Amplification products were detected using agarose gel electrophoresis. In order to identify ATR genomic clones, primers oATR23 (SEQ ID NO: 1) and oATR26 (SEQ ID NO: 2) were employed. To identify CHK1 genomic clones, primer pair MH171 (SEQ ID NO: 5) and MH174 (SEQ ID NO: 7) were used to amplify a 270 base

```
IDH22                                                             SEQ ID NO: 8
NH2-Leu-Lys-Arg-Cys-Thr-Ser-Ser-Asn-Pro-Asn-Gln-Arg-Leu-Pro-Lys-COOH
```

The supernatant, containing the $^{32}$P-labeled peptide was transferred to P81 phosphocellulose paper, the paper was washed three times with 100 mM phosphoric acid (to remove unincorporated label) and once with ethanol, and Cerenkov radiation (in counts per minute, cpm) was counted in a scintillation counter.

Chemical modulators are added to the reaction mixture before the kinase reaction mixture and the effect of the modulator on ATR activity is determined by a change in cpm.

MyoD is a 319 amino acid transcription factor that is often phosphorylated in cells. As described in Example 6 (of WO 97/18323), it has been determined that ATR phosphorylates MyoD in in vitro kinase assays and the target serine residue in myoD has been identified using a MyoD deletion peptide, B-HLH containing amino acids 102 through 165. In view of these observations, two peptides were designed to map more precisely the site of phosphorylation. The first peptide pair CHK1 fragment, and pair MH173 (SEQ. ID NO: 6) and MH174 (SEQ ID NO: 7) were used to amplify a 230 base pair fragment.

```
Primer MH171                    SEQ ID NO: 5
CTCGGTGAATATAGTGCTGC

Primer MH173                    SEQ ID NO: 6
GAGAAGATTATCCTGTCCTG

Primer MH174                    SEQ ID NO: 7
CTTGGTTTCCACCAGATGAG
```

For ATR, genomic YAC clones 941G12, 935A8, 895B8, 941B12, 967H4, and 906F5 were identified. A single genomic BAC encoding ATR, BAC279N71, was identified. For CHK1, genomic YACs 883H1 and 975F11 were identified. All YAC and BAC clones are commercially available from Research Genetics (Huntsville, Ala.).

While the present invention has been described in terms of specific embodiments, it is understood that variations and modifications will occur to those skilled in the art. Accordingly, only such limitations as appear in the appended claims should be placed on the invention.

What is claimed:

1. A method for identifying a compound that promotes differentiation of a differentiation-inhibited cell and inhibits biological activity of a cell cycle checkpoint protein; said method comprising the steps of:

a) comparing expression levels of a differentiation marker protein in said differentiation-inhibited cell in the absence and presence of the compound;

b) comparing biological activity of the cell cycle checkpoint protein in the absence and presence of the compound; and c) identifying the compound as a promoter of differentiation when increased expression of the differentiation marker is detected in step (a) in the presence of the compound and an inhibitor of a cell cycle checkpoint protein when decreased biological activity of the cell cycle checkpoint protein is detected in step (b) in the presence of the compound.

2. The method of claim 1 wherein the differentiation marker protein is selected from the group consisting of myosin heavy chain, MyoD, myogenin and MLC1/3.

3. The method of claim 1 wherein the differentiation marker protein is SCL.

4. The method of claim 1 wherein the differentiation marker protein is selected from the group consisting of MASH, neurogenin, and neuro D.

5. The method of claim 1 wherein the differentiation marker protein is selected from the group consisting of NF-κB and Stat3.

6. The method of claim 1 wherein said cell cycle checkpoint protein is ATR.

7. The method of claim 1 wherein said cell cycle checkpoint protein is CHK1.

* * * * *

UNITED STATES PATENT AND TRADEMARK OFFICE
CERTIFICATE OF CORRECTION

PATENT NO.: 6,071,691

DATED: June 6, 2000

INVENTOR: Hoekstra et al.

It is certified that error appears in the above-identified patent and that said Letters Patent is hereby corrected as shown below:

Column 8, line 18, replace "A" with "An"

Column 8, line 27, replace "and or" with "and/or"

Column 8, line 59, replace "act" with "acts"

Column 8, line 61, after "cell" ($2^{nd}$ occurrence) insert --.--

Column 9, line 12, replace "interests" with "interest"

Column 9, line 42, after "differentiate" insert --.--

Column 9, line 50, replace "Cells" with "cells"

As per IDS/1449 dated 4/13/99 (sheet 4) under Keegan, et al. (pg. 2, column 1, line 2 of entry) replace "meoitically" should be "meiotically"

Column 2, line 39, replace "often" with "of ten"

Column 3, line 60, replace "type" should be "types"

Column 4, line 17, after "degree" and before "of" ($2^{nd}$ occurrence) delete [of]

Column 4, line 60, replace "a" with "an"

Column 6, line 51, replace "include" with "includes"

Column 6, line 65, replace "provide" with "provides"

Column 10, line 17, replace "IOT ½" with "IOT½"

Column 10, line 33, replace "to" (first occurrence in patent line 33) with "the"

Column 11, line 49, replace "neor" with "neo'"

UNITED STATES PATENT AND TRADEMARK OFFICE
CERTIFICATE OF CORRECTION

PATENT NO.: 6,071,691
DATED: June 6, 2000
INVENTOR: Hoekstra et al.

It is certified that error appears in the above-identified patent and that said Letters Patent is hereby corrected as shown below:

Column 12, line 14, after "at" and before "concentrations" delete [a]

Column 12, line 54, replace "Rh30cells" with "Rh30 cells"

Column 13, line 59, replace "Fukaswa" with "Fukasawa"

Column 16, line 30, replace "pcDNA6hiSATR" with "pcDNAhisATR"

Column 17, line 27, replace "3x10$_5$" with "3x10$^5$"

Signed and Sealed this

Seventeenth Day of April, 2001

*Attest:*

NICHOLAS P. GODICI

*Attesting Officer*  *Acting Director of the United States Patent and Trademark Office*

```
                         SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
         (A) LENGTH: 33 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:1:

GACGCAGAAT TCACCAGTCA AAGAATCAAA GAG                                    33

(2) INFORMATION FOR SEQ ID NO:2:

(i) SEQUENCE CHARACTERISTICS:
         (A) LENGTH: 23 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:2:

TGGTTTCTGA GAACATTCCC TGA                                               23

(2) INFORMATION FOR SEQ ID NO:3:

(i) SEQUENCE CHARACTERISTICS:
         (A) LENGTH: 48 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:3:

CGGGATCCAG CATGCATCAC CATCACCATC ACATGGGGGA ACATGGGC                    48

(2) INFORMATION FOR SEQ ID NO:4:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:4:

CATGACCACT GGCCATTCCA CACG                                              24

(2) INFORMATION FOR SEQ ID NO:5:

(i) SEQUENCE CHARACTERISTICS:
         (A) LENGTH: 20 base pairs
         (B) TYPE: nucleic acid
         (C) STRANDEDNESS: single
```

-continued (D) TOPOLOGY: linear (ii) MOLECULE TYPE: DNA (xi) SEQUENCE DESCRIPTION: SEQ ID NO:5:

CTCGGTGAAT ATAGTGCTGC                                            20

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:

GAGAAGATTA TCCTGTCCTG                                            20

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

CTTGGTTTCC ACCAGATGAG                                            20

(2) INFORMATION FOR SEQ ID NO:8:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

Leu Lys Arg Cys Thr Ser Ser Asn Pro Asn Gln Arg Leu Pro Lys
1               5                   10                  15

(2) INFORMATION FOR SEQ ID NO:9:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

Arg Arg Arg Leu Ser Lys Val Asn Glu Ala Phe Glu
1               5                   10